(12) United States Patent
Meng et al.

(10) Patent No.: US 9,091,803 B2
(45) Date of Patent: Jul. 28, 2015

(54) APPARATUS FOR DELIVERY OF LASER-BEAMS OF DIFFERENT WAVELENGTHS TO A FLOW-CYTOMETER

(71) Applicant: Coherent, Inc., Santa Clara, CA (US)

(72) Inventors: Lei Meng, Wilsonville, OR (US); Jordan Wesley Crist, Sherwood, OR (US); Michele Wayne Winz, Woodburn, OR (US); James Schloss, Tigard, OR (US)

(73) Assignee: Coherent, Inc., Santa Clara, CA (US)

( * ) Notice: Subject to any disclaimer, the term of this patent is extended or adjusted under 35 U.S.C. 154(b) by 0 days.

(21) Appl. No.: 14/332,367

(22) Filed: Jul. 15, 2014

(65) Prior Publication Data

US 2015/0077869 A1    Mar. 19, 2015

Related U.S. Application Data (60) Provisional application No. 61/879,062, filed on Sep. 17, 2013.

(51) Int. Cl.
*G02B 17/00* (2006.01)
*G02B 27/14* (2006.01)
*G02B 5/04* (2006.01)
(Continued)

(52) U.S. Cl.
CPC .............. *G02B 5/04* (2013.01); *G01N 21/6486* (2013.01); *G02B 3/06* (2013.01); *G02B 6/28* (2013.01); *G02B 27/0927* (2013.01); *G02B 27/0966* (2013.01); *G02B 27/1006* (2013.01); *G02B 27/126* (2013.01); *G02B 27/144* (2013.01)

(58) Field of Classification Search
CPC .... G02B 5/04; G02B 27/144; G02B 27/1006; G01N 21/6486
USPC .................................. 359/629, 638, 737, 837
See application file for complete search history.

(56) References Cited

U.S. PATENT DOCUMENTS

| 4,826,299 A | 5/1989 | Powell |
| 5,930,600 A | 7/1999 | Seelert et al. |

(Continued)

FOREIGN PATENT DOCUMENTS

| EP | 1403632 A1 | 3/2004 |
| WO | 2010/099118 A1 | 9/2010 |

OTHER PUBLICATIONS

International Search Report and Written Opinion received for PCT Patent Application No. PCT/US2014/046771, mailed on Oct. 17, 2014, 11 pages.

*Primary Examiner* — William Choi
(74) *Attorney, Agent, or Firm* — Morrison & Foerster LLP (57) ABSTRACT

An optical apparatus for delivering to a flow-cell of a flow-cytometer a plurality of beams of laser radiation each thereof having a different wavelength. The apparatus includes a dispersion compensation-prism and a plurality of directing-prisms equal in number to the number of laser-beam. The directing-prisms are arranged to direct the laser radiation beams directly therethrough into the dispersion compensation-prism as converging fan of beams in a first plane. The beams are transmitted by the compensation-prism as a converging fan of beams intersecting then proceeding as a diverging fan of beams in the first plane. A spherical focusing lens is arranged cooperative with a cylindrical lens for focusing the plurality of laser-beams as a plurality of spaced apart elongated focal spots in a plane in which the cytometer flow-cell is located.

18 Claims, 7 Drawing Sheets

(51) Int. Cl.
*G02B 27/09* (2006.01)
*G01N 21/64* (2006.01)
*G02B 3/06* (2006.01)
*G02B 27/10* (2006.01)
*G02B 27/12* (2006.01)
*G02B 6/28* (2006.01)

(56) References Cited

U.S. PATENT DOCUMENTS 8,467,055 B2 * 6/2013 Imanishi et al. ............ 356/344
8,599,487 B2 12/2013 Von Elm et al.
2013/0128365 A1 5/2013 Von Elm et al.

* cited by examiner

APPARATUS FOR DELIVERY OF LASER-BEAMS OF DIFFERENT WAVELENGTHS TO A FLOW-CYTOMETER

PRIORITY

This application claims priority to U.S. Provisional Ser. No. 61/879,062 filed Sep. 17, 2013, the disclosure of which is incorporated by reference.

TECHNICAL FIELD OF THE INVENTION

The present invention relates in general to delivery of laser-beams having different wavelengths into laser-based bio-instruments. The invention relates in particular to delivery of focused laser-beams into a flow-cell of a flow-cytometer.

DISCUSSION OF BACKGROUND ART

A flow-cytometer is a laser based bio-instrument that is employed in cell-counting, cell-sorting, and analysis of biological matter. In the flow-cytometer, a flow-cell carries cells via a sheath fluid. The sheath fluid aligns the cells into a single-file stream thereof. The single-file stream of cells is illuminated via a focused laser-beam. A beam-shaping optic is often employed to enlarge the focused beam in one axis to ensure illumination of the cell. Additionally, the beam-shaping optic can be used to homogenize the laser-beam in the same axis to ensure even illumination of the cells. As the cells pass through the focused laser-beam, laser light is scattered from the beam by the cells. The scattered light is collected by a detector system and analyzed. Results of the analysis are used to determine various properties and statistics, such as size, number, and the type of cells in the flow.

A flow-cytometer can employ fluorophores for facilitating the analysis. The fluorophores are fluorescent chemicals designed to attach to particular sites within the cells. The sites fluoresce when excited by a laser-beam of a particular wavelength, thereby acting like a tracer for the particular sites in which the fluorophores are attached. The fluorescence is collected by the detector system and provides additional data for analysis.

In order to excite multiple fluorophores in the flow-cytometer, multiple laser-beams are focused onto the single-file stream. At the focus, the laser-beams can be spatially separated or overlapped. The detector system of a flow-cytometer typically requires delivery of each focused, different-wavelength laser-beam to a specific location in the flow-cell.

One method of delivery of multiple different-wavelength beams to a flow-cell is by utilizing thin film filters such as dichroic filters. A common practice is to utilize forty-five degree long-pass filters in which shorter wavelengths are reflected from the filter, and longer wavelengths are transmitted through the filter. This technique requires at least one dichroic filter for two wavelengths, and an additional dichroic filter for every additional wavelength.

A problem with filter-based beam-delivery system is that multiple mirrors are often required in order to redirect the beams for focusing into the flow-cytometer. This results in complicated layouts and varied optical path lengths for any particular-wavelength beam. Additionally, each dichroic filter has multiple laser-beams transmitting or reflecting, which creates difficulties in aligning the filters individually and as a group.

As technology in flow-cytometry advances, new fluorophores are developed, which may require laser-beams of additional different wavelengths to be used in a flow-cytometer. A need exists for a beam-delivery system that can be easily customized for new flow-cytometer designs, and for upgrading existing flow-cytometers.

SUMMARY OF THE INVENTION

The present invention is directed to optical apparatus for delivering a plurality of laser-beams, each thereof having a different wavelength, to a cytometer flow-cell. In one aspect the apparatus comprises of a dispersion-compensation prism. A plurality of directing-prisms equal in number to the number of laser-beams in the plurality thereof is provided. The directing-prisms are arranged to transmit the laser radiation beams directly therethrough without internal reflection into the dispersion compensation-prism as converging fan of beams in a first plane. The beams are transmitted by the compensation-prism as a converging fan of beams, intersect, then proceed as a diverging fan of beams in the first plane. A plurality of optical elements including a cylindrical optical element is configured and arranged to focus the diverging fan of laser-radiation beams as a plurality of spaced-apart elongated focal spots at a location in which the cytometer flow-cell is positioned.

BRIEF DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain principles of the present invention.

FIG. 1A is a side-elevation view schematically illustrating details of one preferred embodiment of beam-delivery apparatus in accordance with the present invention, including a converging fan of beams in a first plane, with the beams transmitted by a dispersion-compensation prism (compensation-prism) as a converging fan of beams, intersecting, then proceeding as a diverging fan of beams in the first plane, a cylindrical lens located in the diverging fan of beams, the cylindrical lens having zero optical power in the first plane and finite optical power in a second plane perpendicular to the first plane, and a spherical focusing lens arranged cooperative with the cylindrical lens for focusing the plurality of laser-beams as a plurality of spaced apart elongated focal spots in a plane in which the cytometer flow-cell is located.

DETAILED DESCRIPTION OF THE INVENTION

Figure 1A:
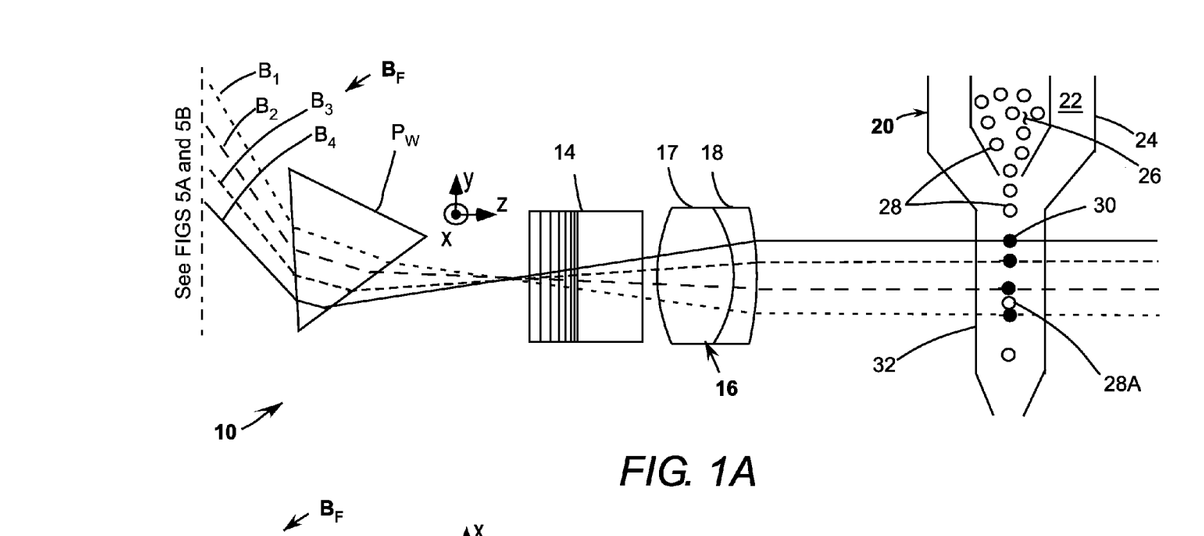
FIG. 1B is a plan view, partly in cross-section, schematically illustrating further detail of the embodiment of FIG. 1A.
Figure 1B:
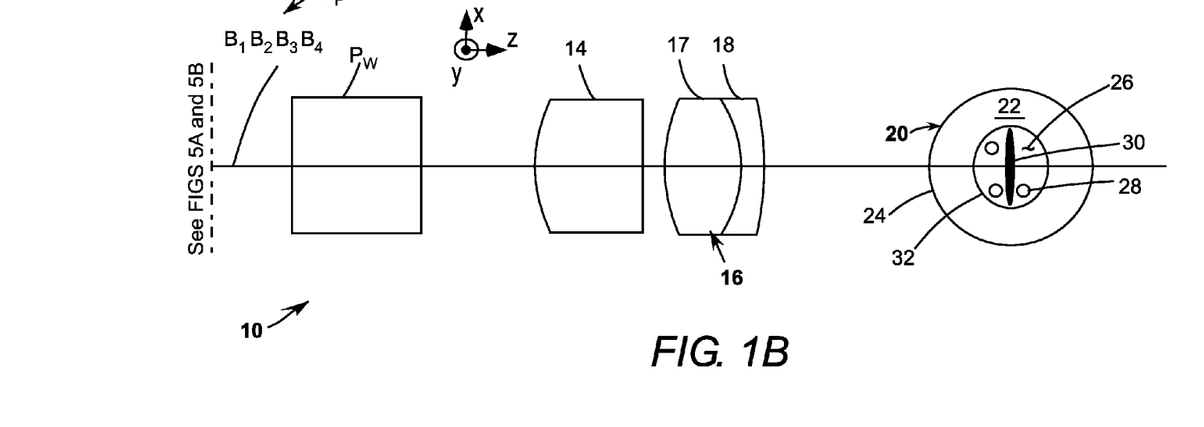

Referring now to the drawings, wherein like components are designated by like reference numerals, FIG. 1A and FIG. 1B schematically illustrates a detail view of an optical train 10, in one preferred embodiment of a laser-beam delivery apparatus in accordance with the present invention. The optical train is characterized by cartesian (mutually perpendicular) axes x, y, and, z with the z-axis indicating the propagation direction of light in the train and x and y being transverse axes.

A beam-fan $B_F$, comprises a plurality of beams of laser-radiation (laser-beams) each thereof having a different wavelength. Here, the beam-fan comprises four laser-beams $B_1$, $B_2$, $B_3$, and $B_4$, each schematically represented by a respective chief ray. The beams are delivered by directing-prisms (not shown), one thereof for each beam. Preferred directing-prism arrangements are described further hereinbelow.

Beam-fan $B_F$ converges in an x-y plane towards a compensation-prism $P_W$. Beam-fan $B_F$ is substantially co-propagating in an x-z plane (see FIG. 1B). The beam-fan is transmitted by compensation-prism $P_W$ as a converging fan of beams which intersect, then proceed as a diverging fan in the y-z plane. Beam-fan $B_F$ passes through a cylindrical lens 14, the cylindrical lens having zero power in the y-z plane and finite optical power in the x-z plane. The beam-fan is focused, in coordination with cylindrical lens 14, by a spherical lens 16, into a cytometer flow-cell 20 as a plurality of spaced-apart, elongated focal spots 30 (see FIG. 1A). Here, spherical lens 16 is a doublet lens consisting of a bi-convex lens 17 in contact with a convex-concave meniscus lens 18 and cylindrical lens 14 is a Powell lens.

A Powell lens is a lens having optical power in only one transverse axis. A Powell lens is configured, in particular for providing (cooperative with other optical elements) uniform intensity-distribution in one transverse axis of an elongated focal spot. A surface providing the optical power is typically acylindrical, i.e., configured according to a complex polynomial. For purposes of this description and the appended claims, the general term "cylindrical lens", as is usual in the optical art, includes lenses such as the Powell lens with an acylindrical surface. Powell lenses are commercially available, custom designed, from a number of commercial suppliers. Such a lens, and an arrangement for using the lens for projecting a line of light, is described in detail in U.S. Pat. No. 4,826,299, the complete disclosure of which is hereby incorporated herein by reference.

Similarly the term "spherical" applied to focusing lens 16 is used in this description and the appended claims in a general sense meaning having the same optical power in both transverse axes. The lens may include one or more elements with one or more aspheric (polynomial-defined) surfaces.

Cytometer flow-cell 20 is generically representative of a cytometer flow-cell configuration. Cytometer flow-cell 20 has a sample of cells 28 in an inner vessel 26. Cells 28 are carried via a sheath-fluid 22 passing through a sheath 24 surrounding vessel 26. Fluid 22 hydro-dynamically focuses the cells into a single-file stream of cells, and directs the single-file stream of cells into a flow-chamber 32. The flow-chamber is made from an optically transparent material, such as fused silica. Flow-cell 20 is positioned relative to lens 16 such that focal spots 30 are in an x-y plane in flow-chamber 32. The single-file stream of cells passes through flow-chamber 32, thereby passing through spaced-apart elongated focal spots 30, as indicated by a cell 28A under observation.

Figure 2A:
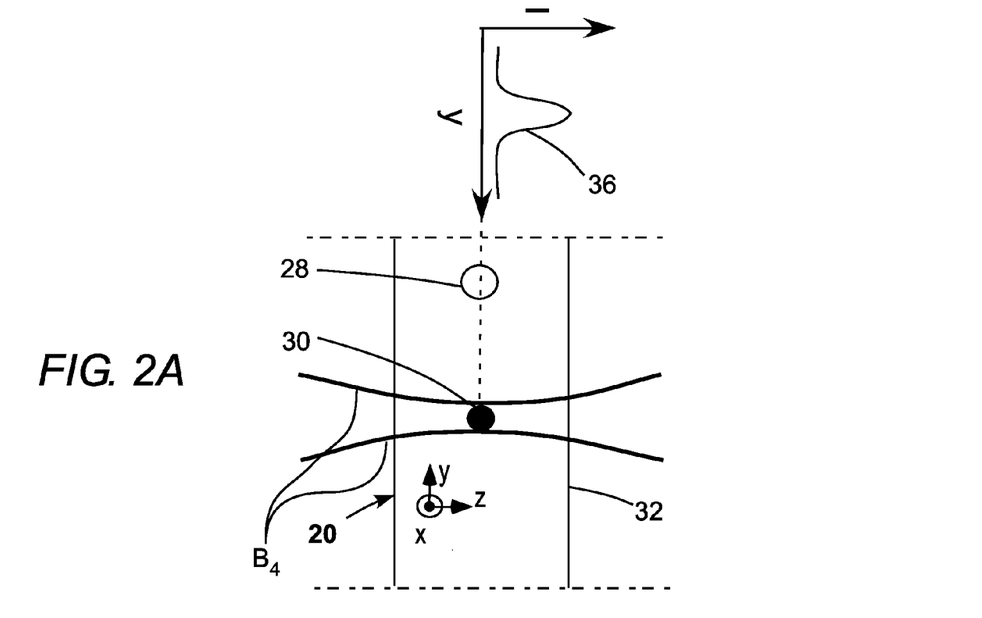
FIG. 2A is a side-elevation view of the cytometer flow-cell of FIG. 1A, schematically illustrating one of the plurality of spaced-apart elongated focal spots in the plane in which the cytometer flow-cell is located.
Figure 2B:
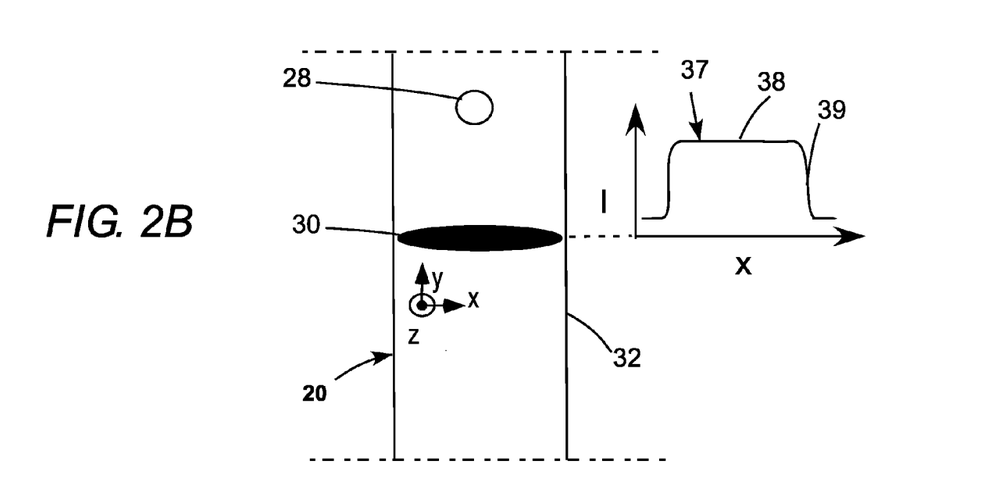
FIG. 2B is an end-elevation view of the cytometer flow-cell of FIG. 1A, partly in cross-section, schematically illustrating further detail of the elongated focal spot of FIG. 2A.

FIG. 2A and FIG. 2B schematically illustrate further detail of one of spaced-apart, elongated focal spots 30 from beam $B_4$ inside flow-chamber 32 of cytometer flow-cell 20. Beam $B_4$ is depicted in FIG. 2A by a hyperbolic envelope characteristic of a focused laser-beam. In the y-z plane, beam $B_4$ enters flow-chamber 32, focusing within the flow-chamber with a Gaussian intensity profile 36. In a y-x plane, the focal spot is elongated in the x-axis with a correspondingly elongated intensity profile 37. Intensity profile 37 has a flat-top 38 and falling (or rising) edges 39, here, spaced in the x-axis by about the width of the flow-chamber.

Figure 3A:
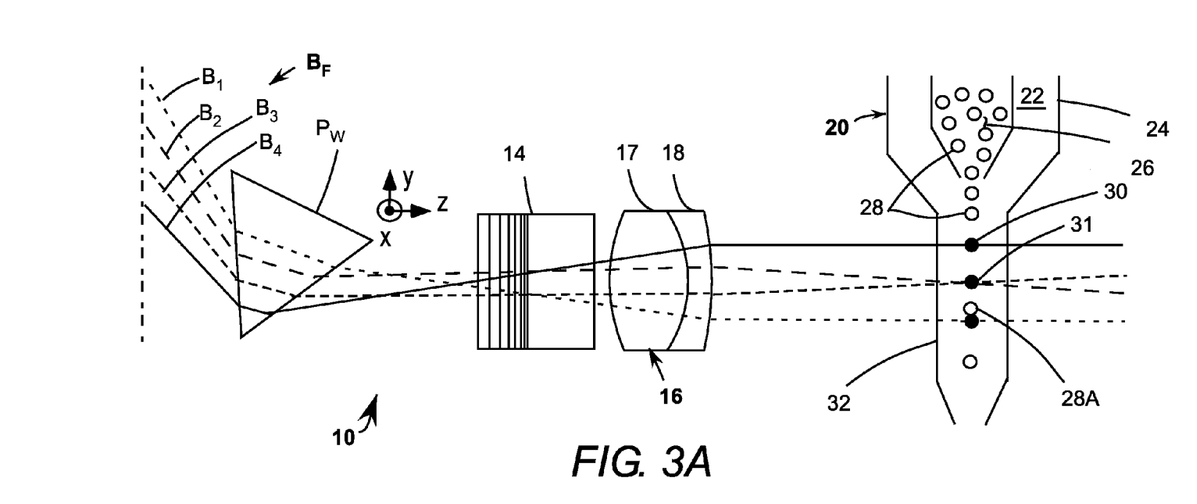
FIG. 3A is a side-elevation view schematically illustrating details of another preferred embodiment of beam delivery apparatus in accordance with the present invention similar to the embodiment of FIG. 1A, but with two elongated focal spots overlapping in the plane in which the cytometer flow-cell is located.
Figure 3B:
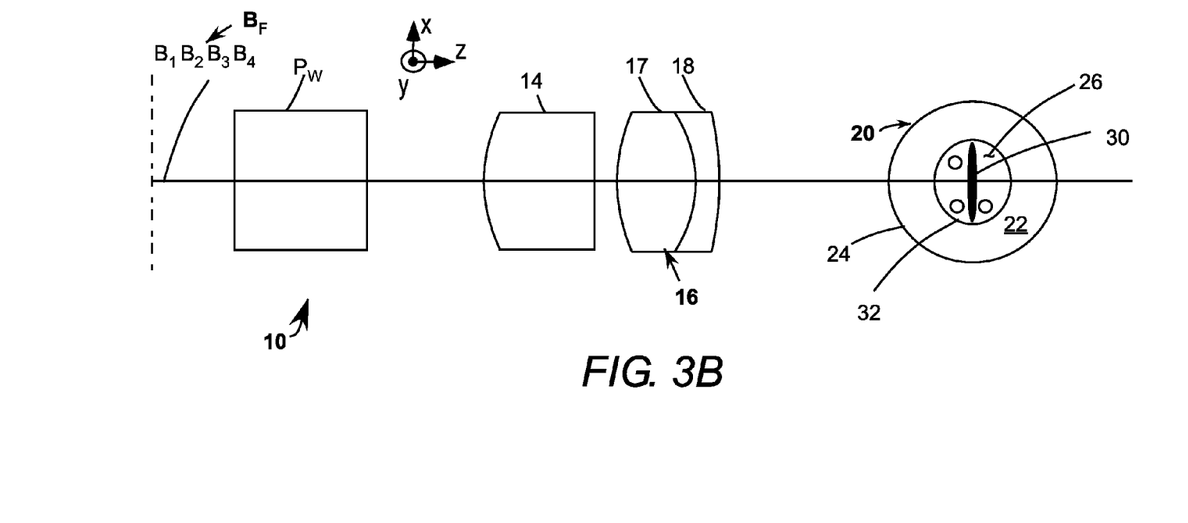
FIG. 3B is a plan-view, partly in cross-section, schematically illustrating further detail of the embodiment of FIG. 3A.

FIG. 3A and FIG. 3B schematically illustrate an alternative focal-spot formation by prism $P_W$ cylindrical lens 14, and spherical lens 16. Here, beam-fan $B_F$, comprising beams $B_1$, $B_2$, $B_3$, and $B_4$, is arranged such that beams $B_2$ and $B_3$ enter optical train 10 at an angle such that the beams propagate in parallel after passing through compensation-prism $P_W$. However, for purposes of this description and the appended claims the term diverging fan of beams applies to cases, such as described here, where some sub-set of the plurality of beams in the fan are parallel to each other.

Beams $B_1$ and $B_4$ focus as spaced apart elongated focal spots 30 within the cytometer flow-cell 20 as described above with reference to FIGS. 2A and 2B. Beams $B_2$ and $B_3$ focus, overlapped, into a common elongated focal spot 31, spaced apart from focal spots 30 of beams $B_1$ and $B_4$. The arrangement of FIGS. 3A and 3B may be used, for example, when a flow-cytometer includes a fluorophore that is preferably excited by two different light-wavelengths.

Figure 4A:
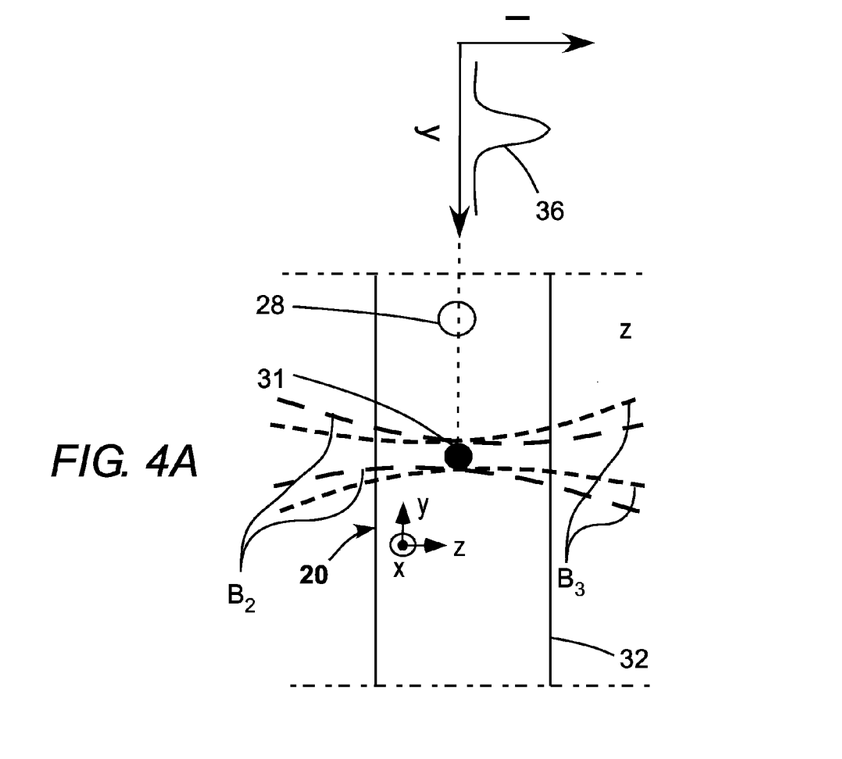
FIG. 4A is a side-elevation view of the cytomer flow-cell of FIG. 3A, schematically illustrating further detail of the overlapping focal spots of FIG. 3A.
Figure 4B:
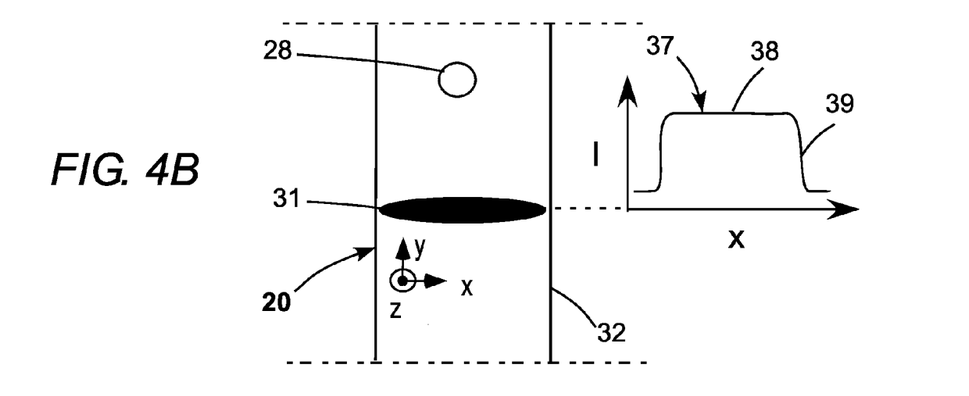
FIG. 4B is an end-elevation view of the cytomer flow-cell, partly in cross-section, schematically illustrating further detail of the overlapping focal spots of FIG. 3A.

FIG. 4A and FIG. 4B schematically illustrate further detail of the common focal spot 31 from beams $B_2$ and $B_3$ inside flow chamber 32 of cytometer flow-cell 20. In the y-z plane, beams $B_2$ and $B_3$ enter flow-chamber 32 overlapping completely at elongated focal spot 31. Common focal spot 31 has Gaussian intensity profile 36 in a y-z plane. In a y-x plane, common focal spot 31 has the elongated flat-top intensity profile as described above with reference to FIG. 2B.

Figure 5A:
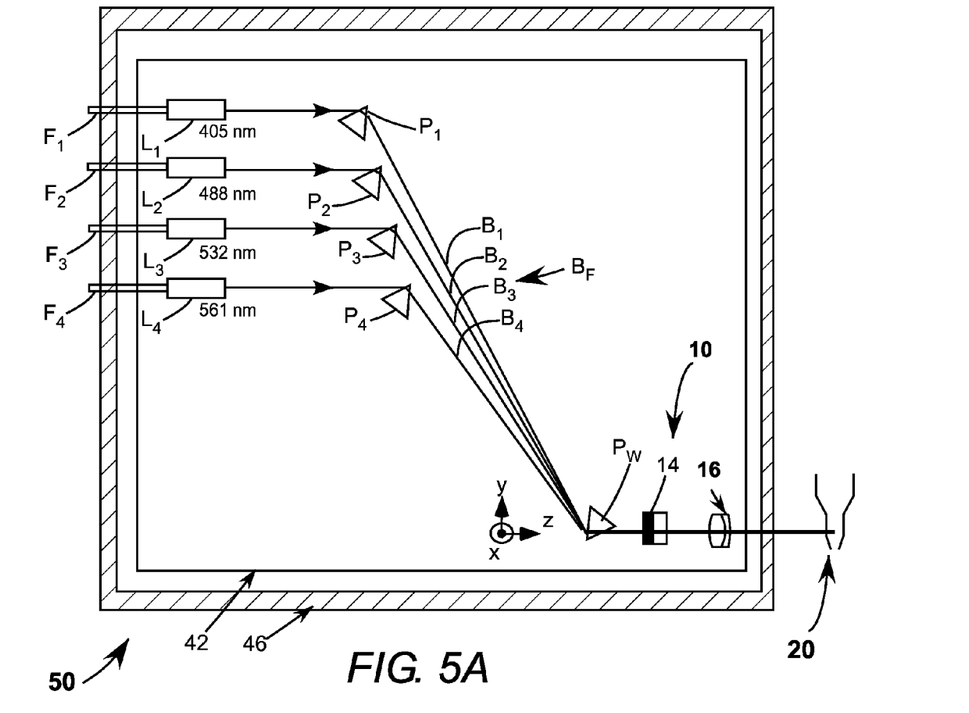
FIG. 5A is a side-elevation view, schematically illustrating a preferred arrangement of four directing-prisms delivering four different-wavelength laser-beams to the compensation-prism in the embodiment of FIGS. 1A and 1B.
Figure 5B:
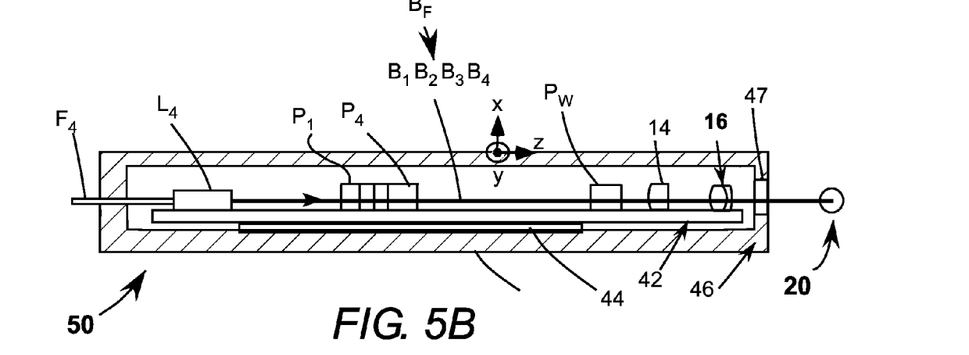
FIG. 5B is a plan view, partly in cross-section, schematically illustrating further detail of the directing-prism arrangement of FIG. 5A.

FIG. 5A and FIG. 5B schematically illustrates a preferred embodiment of 50 optical apparatus for delivering laser-beams $B_1$, $B_2$, $B_3$, and $B_4$ to optics train 10 described above with reference to FIGS. 1A and 1B. Those skilled in the art will recognize that the scale of FIGS. 5A and 5B precludes depicting the detail of FIGS. 1A and 1B.

In apparatus 50, collimating lenses $L_1$, $L_2$, $L_3$, and $L_4$ produce laser-beams $B_1$, $B_2$, $B_3$, and $B_4$ from, respectively, output of optical fibers $F_1$, $F_2$, $F_3$, and $F_4$ These fibers, of course, carry laser-radiation from separate lasers (not shown) providing laser-radiation at the different wavelengths required.

The optical fibers are preferably single-mode polarization-maintaining fibers, arranged such that the polarization-orientation of the beams is parallel to the y-axis of FIG. 5A. Here, by way of example, the wavelengths of laser-beams $B_1$, $B_2$, $B_3$, and $B_4$ are assumed to be 405 nanometers (nm), 488 nm, 532 nm, 561 nm, respectively.

The laser-beams are delivered from lenses $L_1$, $L_2$, $L_3$, and $L_4$, such that each one is incident on a face of a corresponding one of prisms $P_1$, $P_2$, $P_3$, and $P_4$, which can be referred to as directing-prisms. The prisms are arranged spaced apart in a direction at an angle to the propagation direction of the laser-beams. The directing-prisms are also arranged such that the beams are incident thereon at about the minimum-deviation angle. The prisms are preferably all of equal dimensions, made from the same suitable glass, and with the bases of the prisms parallel to each other. One suitable glass is N-SF11 which has a high refractive index and relatively high dispersion. This provides that the prisms can be equal angle)(60° prisms with minimum-deviation beam-incidence thereon near the Brewster angle to minimize losses for y-axis aligned polarized radiation without a need for anti-reflection coating.

The different wavelength beams are transmitted through directing-prisms $P_1$, $P_2$, $P_3$, and $P_4$ without internal reflection and turned by the directing-prisms to form beam-fan $B_F$ (in the y-z plane of the drawing only) that converges onto compensation-prism $P_W$. Compensation-prism $P_W$ substantially compensates dispersion introduced in the laser-beams by transmission through the directing-prisms.

The compensation-prism is preferably of the same dimensions and material as the directing-prisms and is arranged with the combining apex thereof opposed to the apexes of the directing-prisms, but with the base thereof parallel to the bases of the directing-prisms. The distance between the directing-prisms and compensation-prism $P_W$ is selected such that prism $P_W$ directs the different-wavelength beams at slightly different angles into optical train 10 in order to achieve the desired spatial separation within cytometer flow-cell 20 as described above.

The focal length of collimating lenses $L_1$, $L_2$, $L_3$, and $L_4$ can be chosen, with respect to the focal length of the focusing optic to achieve a desired size at the flow-cell. Each of the collimating lenses may be configured to be the same, or configured individually to compensate for variation of the numerical aperture (NA) of the optical fibers. The collimating lenses can also be positioned with respect to the optical fibers such that chromatic shift of the focus of focusing lens 16 can be compensated, and all different wavelengths will focus in the same plane, i.e., the focal spots will be exactly co-planar.

It will be evident from the drawing of FIG. 1A that using individual prisms for directing individual beams being directed allows the prism apexes to intrude marginally into the beam-fan at widely spaced points along the fan which provides for a wide separation of input laser-beams without a long beam-path. The arrangement has other advantages in manufacturing, as all prisms have the same dimensions, are of the same material, and do not need to be anti-reflection coated if y-axis polarized light is transmitted by the prisms and the prisms are aligned at about the minimum deviation angle as described above.

The directing-prisms, the compensation-prism and the optical train 10 can all be bonded to a common base-plate 42, after being aligned. Alignment can be effected by a suitable cut-out mask or jig. One suitable method for solder-bonding optical components is described in U.S. Pat. No. 5,930,600, assigned to the assignee of the present invention, and the complete disclosure of which is hereby incorporated herein by reference. Baseplate 42 can then be attached to a housing 46 by mounting plate 44. An optional transparent window 47 can be utilized to seal the housing. See also U.S. Pat. No. 8,599,487, incorporated by reference, which utilizes prisms to combine and direct multiple wavelength beams into a single fiber output.

Apparatus 50 is described above in terms of one general arrangement of laser-beams, directing-prisms, compensating prism and focusing optics. From the description of the present invention provided herein one skilled in the art can design particular configurations by reverse ray-tracing the desired system, starting with spatially separated focal positions and tracing back through the entire optical train of the apparatus to determine the exact position and angles of prisms and fiber-spacing (beam-spacing). Such ray tracing can be done using commercially available optical design software, such as ZEMAX available from the Zemax Corporation, of Belleview, Wash.

Figure 6A:
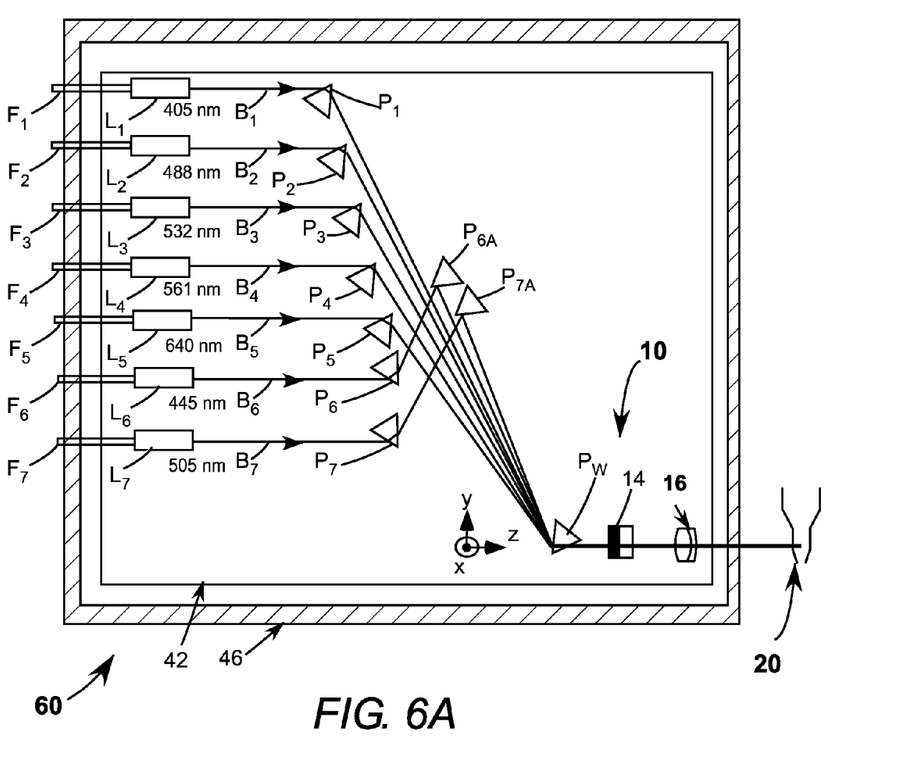
FIG. 6A is a plan view from above, schematically illustrating a preferred arrangement of seven directing-prisms delivering seven different-wavelength laser-beams to the compensation-prism in the embodiment of FIGS. 1A and 1B.
Figure 6B:
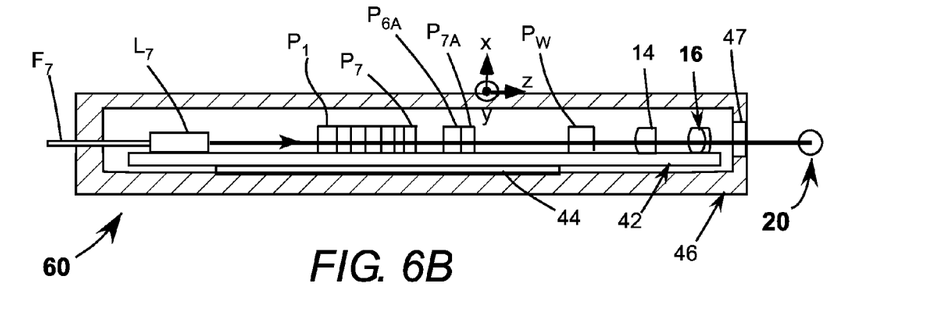
FIG. 6B is a side-elevation view from above, schematically illustrating further detail of the directing-prism arrangement of FIG. 6A.

FIG. 6A and FIG. 6B schematically illustrate another preferred embodiment 60 of laser-beam delivery apparatus in accordance with the present invention. Apparatus 60 is similar to apparatus 50 of FIGS. 5A and 5B with an exception that three additional beams $B_5$, $B_6$, and $B_7$ are delivered to flow-cytometer 20. These beams are assumed to have exemplary wavelengths 640 nm, 445 nm, and 505 nm respectively. Consistent with the addition of three additional beams a corresponding three delivery fibers $F_5$, $F_6$, and $F_7$, a corresponding three collimating lenses $L_5$, $L_6$, and $L_7$, and a corresponding three directing-prisms $P_5$, $P_6$, and $P_7$ are added.

Beam $B_5$ transmits through directing-prism $P_5$ directly to prism $P_W$ as described above for beams $B_1$, $B_2$, $B_3$, and $B_4$, and directing-prisms $P_1$, $P_2$, $P_3$, and $P_4$. Beams $B_6$ and $B_7$ utilize directing-prisms $P_6$ and $P_7$, respectively, to transmit the beams towards reflecting prisms $P_{6A}$ and $P_{7A}$, respectively. In order to effect this, the apexes of directing-prisms $P_6$ and $P_7$ are rotated clockwise by about 60° relative to the apexes of prisms $P_1$ through $P_5$, as indicated in FIG. 6A. Prisms $P_{6A}$ and $P_{7A}$ then reflect respective beams towards compensation-prism $P_W$ as part of a converging fan of beams.

In theory at least, conventional (parallel-sided) mirrors could be substituted for prisms $P_{6A}$ and $P_{7A}$. This is difficult in practice, however, because of potential problems in aspect-ratio (rigidity), and potential problems in mounting. The use of faces of the prisms as mirrors (using a prism as a mirror substrate) provides that the mirror substrate is rigid, and can be manufactured in a same batch as directing-prisms. The side of the prisms is convenient for bond-mounting and alignment on base-plate 42. Further, the apex of the prism allows beam-turning to be accomplished with a close physical spacing of the beams to be combined. In practice, the apex of any of the prisms does not need to be a "knife-edge" as depicted, but can be slightly flattened, while still being describable as an "apex" for purposes of this description and the appended claims.

Figure 7A:
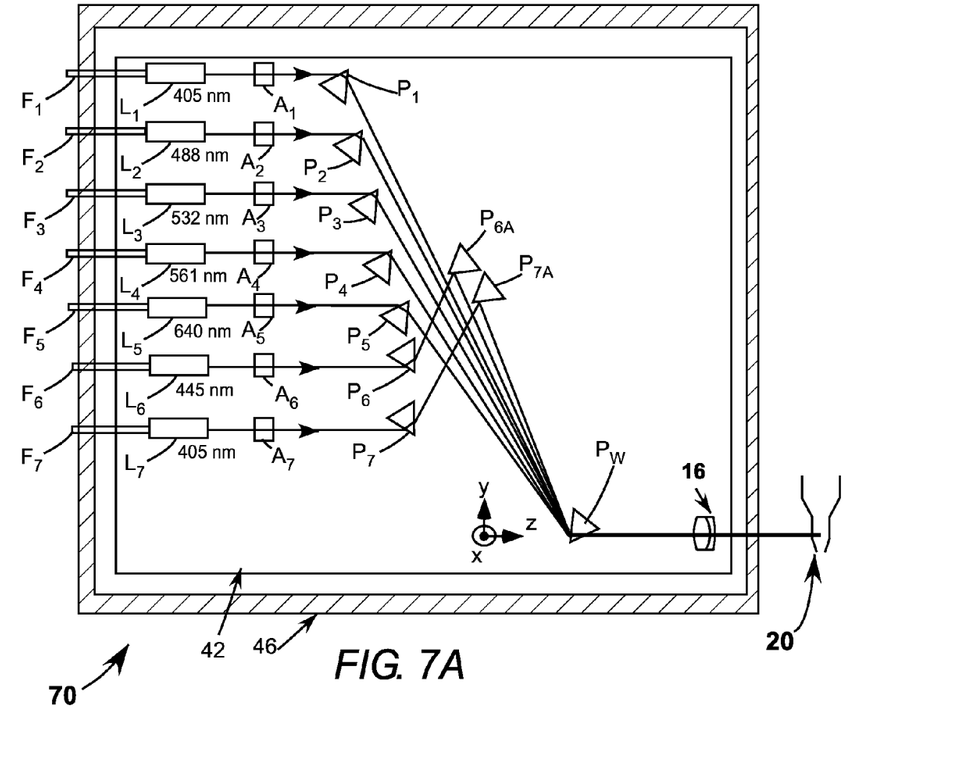
FIG. 7A is a plan view from above, of a beam-delivery apparatus in accordance with the present invention similar to the apparatus of FIGS. 1A, 1B, 6A, and 6B but wherein the cylindrical lens in the diverging fan of beams is replaced by a plurality of cylindrical lenses, one in a path of each of the laser-beams to a corresponding directing-prism.
Figure 7B:
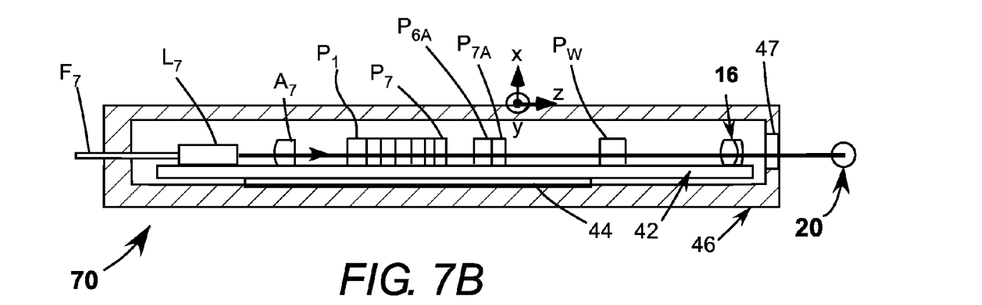
FIG. 7B is a side-elevation view schematically illustrating further detail of the cylindrical-lens and directing-prism arrangement of FIG. 7A.

FIG. 7A and FIG. 7B schematically illustrate another preferred embodiment 70 of laser-beam delivery apparatus in accordance with the present invention. Apparatus 70 is similar to apparatus 60 of FIGS. 6A and 6B with an exception that (common) cylindrical lens 14 of apparatus 60 is replace in apparatus 70 by independent cylindrical lenses $A_1$, $A_2$, $A_3$, $A_4$, $A_5$, $A_6$, and $A_7$ in the path of beams $B_1$, $B_2$, $B_3$, $B_4$, $B_5$, $B_6$, and $B_7$ to the corresponding directing-prisms.

As the wavelength-range of the plurality of beams increases, it becomes increasingly difficult to design common cylindrical lens 14 cooperative with focusing lens 16 to locate focal spots of the beams in the same plane on the z-axis, and also to optimize (in particular) the intensity distribution in each of the focal spots. This is particularly the case if it is desired that lens 14 be a Powell lens. Providing individual cylindrical lenses as depicted in FIGS. 7A and 7B allows independent manipulation of each of the beams. With the independent cylindrical lenses, added flexibility for manipulation of individual laser-beams is allowed to achieve a more perfect flat-top for each channel of different elongation of the focal spots. Variation in the NA of the fibers may result in different beam sizes and require a distinct design for each of cylindrical lenses $A_1$, $A_2$, $A_3$, $A_4$, $A_5$, $A_6$, and $A_7$. Such designs can be made using commercially available ray-trace software as discussed above.

Those skilled in the art to which the present invention pertains will recognize that while above-described embodiments of the inventive beam-delivery apparatus are exemplified using beams of particular wavelengths, beams of other wavelengths may be combined using these embodiments without departing from the spirit and scope of the present invention. Further, while embodiments of the present invention are described above with laser-beams delivered by optical fibers, the invention is equally applicable to beams delivered directly from diode-lasers.

In summary, the present invention is described above in terms of particular embodiments. The invention, however, is not limited to the embodiments described and depicted herein. Rather, the invention is limited only by the claims appended hereto.

What is claimed is:

1. Optical apparatus for delivering to a flow-cell of a flow-cytometer a plurality of beams of laser radiation, each thereof having a different wavelength, the apparatus comprising:
    a dispersion-compensation prism;
    a plurality of directing-prisms equal in number to the number of laser-beams in the plurality thereof, the directing-prisms arranged to transmit the laser radiation beams directly therethrough, without internal reflection, and direct the laser-radiation beams into the dispersion compensation-prism, as a converging fan of beams in a first plane, with the beams transmitted by the dispersion-compensation prism as a converging fan of beams intersecting then proceeding as a diverging fan of beams in the first plane; and
    a plurality of optical elements including a cylindrical optical element, the plurality of optical elements configured and arranged to focus the diverging fan of laser-radiation beams as a plurality of spaced-apart elongated focal spots at a location in which the cytometer flow-cell is positioned.

2. The apparatus of claim 1, wherein the cylindrical lens element has zero optical power in the first plane and finite optical power in a second plane perpendicular to the first plane.

3. The apparatus of claim 2, wherein all other optical elements in the plurality thereof are spherical lens elements.

4. The apparatus of claim 1, wherein the spaced-apart elongated focal spots are about coplanar at the location in which the cytometer flow-cell is positioned.

5. The apparatus of claim 1, wherein the cylindrical lens element is a Powell lens element.

6. The apparatus of claim 1, wherein the plurality of beams of laser-radiation are collimated before being transmitted by the directing-prisms.

7. The apparatus of claim 1, wherein there are at least four laser-beams in the plurality thereof providing at least four elongated focal spots and at least two of the elongated focal spots overlap, spaced apart from the other elongated focal spots.

8. The apparatus of claim 1, further including a plurality of optical fibers and a corresponding plurality of collimating lenses arranged to deliver the plurality of beams of laser radiation to the directing-prisms.

9. The apparatus of claim 8, wherein the spaced-apart elongated focal spots are about coplanar at the location in which the cytometer flow-cell is positioned.

10. The apparatus of claim 9, wherein the plurality of collimating lenses are identical and individually positioned with respect to each of the respective plurality of optical fibers to achieve the coplanar focus at the location in which cytometer flow-cell is positioned.

11. The apparatus of claim 9, wherein each of the plurality of collimating lenses are individually configured with respect to each of the plurality of optical fibers to achieve the coplanar focus at the location in which the cytometer flow-cell is positioned.

12. The apparatus of claim 1, wherein in the plurality of optical elements there is one cylindrical lens element two spherical elements.

13. The apparatus of claim 11, where one of the spherical elements has negative optical power and the other spherical element has positive optical power.

14. Optical apparatus for delivering to a flow-cell of a flow-cytometer a plurality of beams of laser radiation, each thereof having a different wavelength, the apparatus comprising:
    a first plurality of cylindrical optical elements equal in number to the number of laser beams, each thereof arranged to receive and transmit a corresponding one of the laser-beams;
    a dispersion-compensation prism;
    a plurality of directing-prisms equal in number to the number of laser-beams in the plurality thereof, the directing-prisms arranged to receive the laser beams from a corresponding one of the first plurality of cylindrical lenses and transmit the laser radiation beams directly therethrough, without internal reflection, and direct the laser-radiation beams into the dispersion compensation-prism, as converging fan of beams in a first plane, with the beams transmitted by the dispersion-compensation prism as a converging fan of beams intersecting then proceeding as a diverging fan of beams in the first plane; and
    a second plurality of optical elements cooperative with the first plurality of optical elements, the first and second pluralities of optical elements configured and arranged to focus the diverging fan of laser-radiation beams as a plurality of spaced-apart elongated focal spots at a location in which the cytometer flow-cell is positioned.

15. The apparatus of claim 14, wherein the cylindrical lens elements in the first plurality thereof have zero optical power in the first plane and finite optical power in a second plane perpendicular to the first plane.

16. The apparatus of claim 15, wherein all optical elements in the second plurality thereof are spherical lens elements.

17. The apparatus of claim 14, wherein the spaced-apart elongated focal spots are about coplanar at the location in which the cytometer flow-cell is positioned.

18. The apparatus of claim 14, wherein all cylindrical lens elements in the first plurality thereof are Powell lens elements.

* * * * *